United States Patent
Koktzoglou et al.

(10) Patent No.: US 10,362,961 B2
(45) Date of Patent: Jul. 30, 2019

(54) SYSTEM AND METHOD FOR NEUTRAL CONTRAST MAGNETIC RESONANCE IMAGING OF CALCIFICATIONS

(71) Applicants: Ioannis Koktzoglou, Des Plaines, IL (US); Robert R. Edelman, Highland Park, IL (US)

(72) Inventors: Ioannis Koktzoglou, Des Plaines, IL (US); Robert R. Edelman, Highland Park, IL (US)

(73) Assignee: NORTHSHORE UNIVERSITY HEALTHSYSTEM, Evanston, IL (US)

( * ) Notice: Subject to any disclaimer, the term of this patent is extended or adjusted under 35 U.S.C. 154(b) by 460 days.

(21) Appl. No.: 14/593,446

(22) Filed: Jan. 9, 2015

(65) Prior Publication Data

US 2015/0196223 A1     Jul. 16, 2015

Related U.S. Application Data

(60) Provisional application No. 61/925,997, filed on Jan. 10, 2014.

(51) Int. Cl.
    *A61B 5/00*       (2006.01)
    *A61B 5/055*     (2006.01)
    *A61B 5/02*       (2006.01)

(52) U.S. Cl.
    CPC .......... *A61B 5/055* (2013.01); *A61B 5/02007* (2013.01); *A61B 2576/02* (2013.01)

(58) Field of Classification Search
    CPC ..... A61B 5/055; A61B 5/4514; A61B 5/4528; A61B 5/1078; A61B 5/4585; A61B 5/4836
See application file for complete search history.

(56) References Cited

U.S. PATENT DOCUMENTS

| | | | |
|---|---|---|---|
| 2002/0177770 A1* | 11/2002 | Lang ............. | A61B 5/055 600/410 |
| 2007/0015995 A1* | 1/2007 | Lang ............. | A61B 5/055 600/407 |
| 2007/0038073 A1* | 2/2007 | Mistretta ....... | A61B 5/055 600/410 |

(Continued)

OTHER PUBLICATIONS

Cai, Jian-Ming, et al. "Classification of human carotid atherosclerotic lesions with in vivo multicontrast magnetic resonance imaging." Circulation 106.11 (2002): 1368-1373.

(Continued)

*Primary Examiner* — Joel Lamprecht
(74) *Attorney, Agent, or Firm* — Quarles & Brady LLP

(57) ABSTRACT

Systems and methods for magnetic resonance imaging ("MRI"), in which accurate and conspicuous visualization of vascular calcifications and other bony structures can be achieved. An MRI system is operated to perform a pulse sequence that generates substantially similar signal intensity from soft tissues (e.g. muscle, fat, blood) within the body. For instance, blood can be rendered to have a signal intensity that is substantially similar to the vessel wall, while fat and muscle are rendered to appear substantially similar to the vessel wall. With this "neutral" contrast, arterial calcifications, which appear dark due to their low proton density, can be more readily and efficiently visualized by an interpreting physician.

15 Claims, 3 Drawing Sheets

(56) References Cited

U.S. PATENT DOCUMENTS

| | | | | |
|---|---|---|---|---|
| 2007/0078333 A1* | 4/2007 | Abe | ............ | G01R 33/5601 |
| | | | | 600/420 |
| 2010/0256480 A1* | 10/2010 | Bottomley | ......... | G01R 33/285 |
| | | | | 600/411 |
| 2011/0245650 A1* | 10/2011 | Kerwin | ............ | G01R 33/5635 |
| | | | | 600/407 |
| 2012/0105060 A1* | 5/2012 | Boulant | ............ | G01R 33/4828 |
| | | | | 324/309 |
| 2015/0139514 A1* | 5/2015 | Mohr | ............ | G06T 5/50 |
| | | | | 382/131 |

OTHER PUBLICATIONS

Koktzoglou, Ioannis. "Gray blood magnetic resonance for carotid wall imaging and visualization of deep-seated and superficial vascular calcifications." Magnetic resonance in medicine 70.1 (2013): 75-85.

Chan, Cheuk F., et al. "Ultra-short echo time cardiovascular magnetic resonance of atherosclerotic carotid plaque." Journal of Cardiovascular Magnetic Resonance 12.1 (2010): 17.

* cited by examiner

SYSTEM AND METHOD FOR NEUTRAL CONTRAST MAGNETIC RESONANCE IMAGING OF CALCIFICATIONS

CROSS-REFERENCE TO RELATED APPLICATIONS

This application claims the benefit of U.S. Provisional Patent Application Ser. No. 61/925,997, filed on Jan. 10, 2014, and entitled "SYSTEM AND METHOD FOR NEUTRAL CONTRAST MAGNETIC RESONANCE IMAGING OF CALCIFICATIONS."

STATEMENT REGARDING FEDERALLY SPONSORED RESEARCH

This invention was made with government support under R01HL096916 awarded by the National Institutes of Health. The government has certain rights in the invention.

BACKGROUND OF THE INVENTION

The field of the invention is systems and methods for magnetic resonance imaging ("MRI"). More particularly, the invention relates to systems and methods for imaging vascular calcifications or bony structures.

Vascular calcifications are a major component of atherosclerotic disease, and are often used for quantifying arterial disease as well as assessing risk for future cardiovascular morbidity and mortality. In clinical practice, computed tomography ("CT") is used to visualize and quantify vascular calcifications. CT, however, involves the use of potentially harmful ionizing radiation and, thus, is not well suited for longitudinal and/or serial assessments of atherosclerotic disease, or for screening of the general population. MRI is a promising modality for visualizing and quantifying atherosclerosis without the safety concerns of ionizing radiation. Existing MRI techniques, however, cannot clearly and rapidly visualize arterial calcifications in patients with atherosclerotic disease.

A few approaches have been proposed for identifying vascular calcifications with MRI. One method referred to as "multi-contrast" (Cai J M et al. Circulation. 2002 Sep 10; 106(11):1368-73), includes the acquisition of a dark-blood T1-weighted fast spin echo ("FSE") scan, a dark-blood T2-weighted FSE scan, a dark-blood spin-density weighted FSE scan, and a bright-blood time-of-flight ("TOF") scan. This multi-contrast approach identifies vascular calcifications based on their dark appearance on all four acquisitions. Limitations of this approach include long scan times associated with multiple (typically four) scans, poor spatial resolution (because the FSE techniques are multi-slice 2D techniques and not 3D), and artifacts in the TOF imaging, such as arterial inhomogeneity and saturation. Furthermore, interpretation of multiple image sets is time consuming and can be significantly impaired due to patient motion in one or more of the scans.

Another approach for visualizing calcifications involves the use of 3D dark blood acquisitions (either FSE or gradient-echo), which provide images that depict the arterial wall. Although these techniques can visualize vascular calcifications based on their dark appearance in relation to the adjacent vascular wall, many other structures within the field of view appear dark, including the arterial lumen and perivascular fat. The presence of a considerable amount of dark-appearing perivascular fat renders vascular calcifications less conspicuous. With 3D dark blood techniques, superficial vascular calcifications are particularly difficult to discern because they are indistinguishable from the dark lumen. The offshoot technique of "gray-blood imaging" (Koktzoglou I, Magn Reson Med. 2013 July; 70(1):75-85), solves the poor contrast between superficial vascular calcifications and the vascular lumen, but does not solve the issue of poor contrast between perivascular fat.

In another recent approach, described by Q. Yang, et al., in "Imaging the Vessel Wall in Major Peripheral Arteries using Susceptibility Weighted Imaging," *J Magn Reson Imaging*, 2009; 30:357-365, susceptibility-weighted imaging ("SWI") was used in an effort to detect calcifications on the basis of their increased diamagnetic susceptibility. Although this technique shows some promise, it can be difficult to reliably obtain accurate phase maps, which are required for SWI, near peripheral vessels due to the presence of blood flow, fat-water interfaces, and bony structures that all produce additional phase shifts. An additional drawback of SWI for imaging calcifications is that it requires extensive offline image processing.

In light of the foregoing, there remains a need to provide systems and methods for accurately and reliably imaging vascular calcifications with MRI. It would therefore be desirable to provide systems and methods that can obtain images that conspicuously depict vascular calcifications without the drawbacks in scan time, spatial resolution, and artifacts associated with currently available techniques.

SUMMARY OF THE INVENTION

The present invention overcomes the aforementioned drawbacks by providing systems and methods for "neutral contrast" magnetic resonance imaging ("NCI") that provide for fast and accurate visualization of arterial calcifications.

It is an aspect of the invention to provide a method for producing an image of a subject using a magnetic resonance imaging ("MRI") system. The MRI system is directed to generate a radio frequency ("RF") excitation field to excite spins in an imaging volume. This RF excitation field has a flip angle in a range from about an Ernst angle for blood to about an Ernst angle for muscle. The MRI system is then directed to acquire data at an echo time at which spins associated with water are substantially in-phase with spins associated with fat. An image is then reconstructed from the acquired data. In this image, soft tissues have a substantially similar image intensity value and calcifications have an image intensity value that is significantly different that the image intensity values of the soft tissues.

The foregoing and other aspects and advantages of the invention will appear from the following description. In the description, reference is made to the accompanying drawings that form a part hereof, and in which there is shown by way of illustration a preferred embodiment of the invention. Such embodiment does not necessarily represent the full scope of the invention, however, and reference is made therefore to the claims and herein for interpreting the scope of the invention.

DETAILED DESCRIPTION OF THE INVENTION

Figure 1A:
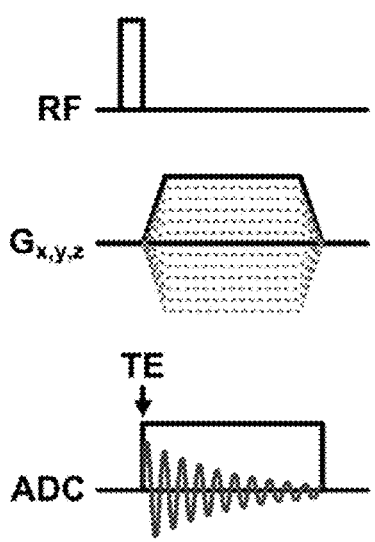
FIG. 1A is an example of a pulse sequence for acquiring data with substantially neutral contrast between soft tissues using a 3D radial acquisition with an ultra-short echo time.

Described here are systems and methods for magnetic resonance imaging ("MRI"), in which accurate and conspicuous visualization of vascular calcifications and other bony structures can be achieved. An MRI system is operated to perform a pulse sequence that generates substantially similar signal intensity from soft tissues (e.g. muscle, fat, blood) within the body. That is, the pulse sequence is designed to produce a neutral image contrast between soft tissues in the subject's body. For instance, blood can be rendered to have a signal intensity that is substantially similar, or hyperintense, to the vessel wall, while fat and muscle are rendered to appear substantially similar to the vessel wall. With this "neutral" contrast, arterial calcifications, which appear dark due to their low proton density, can be more readily and efficiently visualized by an interpreting physician.

The systems and methods of the present invention permit fast and accurate visualization of vascular calcifications with a single acquisition. As a result, multiple scans are not required, which reduces the overall scan time and inconvenience to the subject being imaged. The systems and methods of the present invention also acquire images without the confounding appearance of other tissues.

In general, the NCI technique includes acquiring data such that the contrast between soft tissues is low while the contrast between calcifications and soft tissues is relatively high. For instance, the soft tissues can have a first contrast and the calcifications, which may include bony structures, generally, can have a second contrast that is greater than the first contrast. As an example, the soft tissues can include water, fat, and muscle tissue. In this example, the water, fat, and muscle tissues will have substantially similar image intensity levels in the reconstructed image, thereby rendering these tissues to have very low contrast with respect to each other. Calcifications or other bony structures, however, will have signal intensity levels that are significantly different than the soft tissues; thus, the calcifications or other bony structures will have higher contrast than the soft tissues.

Because of the range of tissue types across the imaging volume, it can be particularly challenging to ensure that all soft tissues appear different from the calcifications or bony structures. For example, ligaments, tendons, and fascia all appear dark with standard MRI acquisition methods; however, calcifications also appear dark in these standard acquisitions. Moreover, chemical shift artifacts at the boundary between fat and water-dominated tissue (e.g., muscle) also appear dark. Any low-signal tissues will obscure vascular calcifications in these standard images and thus will undermine diagnostic accuracy.

To address these problems, the neutral contrast of soft tissues is achieved using a pulse sequence that includes a radio frequency ("RF") excitation having a flip angle in a range having a lower bound at or near the Ernst angle for blood and an upper bound at or near the Ernst angle for muscle tissue, and in which data are acquired while water and fat spins are in-phase. The combination of these two features results in the water, fat, and muscle tissues having substantially similar signal intensity levels, and thus very low contrast relative to each other, in the reconstructed image. On the contrary, calcifications and other bony structures will have significantly different image intensity levels than the soft tissues and, thus, will have appreciably high contrast relative to the soft tissues.

In some embodiments of NCI, a three-dimensional gradient-echo sequence positioned along the length of the arterial, or other vascular, anatomy under interrogation is executed with a flip angle near the Ernst angle for muscle. Although 3D imaging is preferred because it supports the acquisition of very high spatial resolution, 2D NCI is also feasible. To avoid signal phase cancellation at fat-water interfaces, an in-phase echo time is used, as noted above.

In some embodiments, flow compensation can be used to minimize artifacts from flowing blood. As an example, flow compensation can be used to minimize intravoxel phase shifts associated with flowing spins, such as those attributable to blood. For instance, these phase shifts can be minimized to a value less than about pi/4 radians.

Figure 1B:
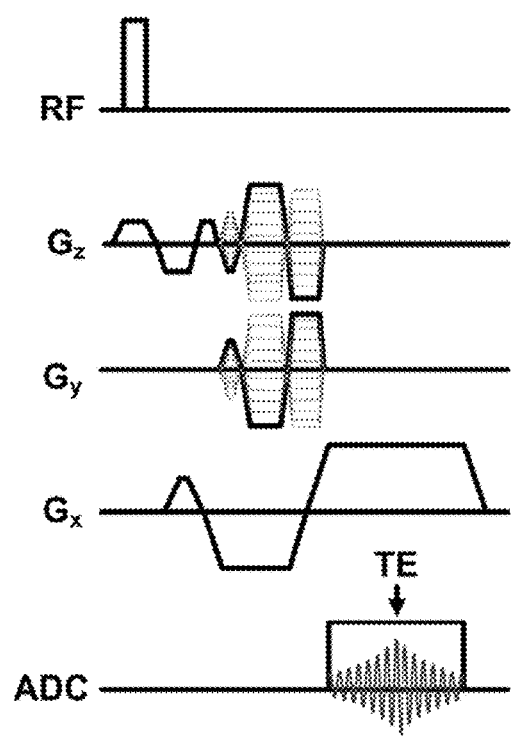
FIG. 1B is an example of a pulse sequence for acquiring data with substantially neutral contrast between soft tissues using a 3D Cartesian acquisition with flow-compensation gradients.

Flow compensation can be achieved, for example, using an ultra-short echo time acquisition, using a zero echo time acquisition, or by establishing flow-compensation magnetic field gradients prior to data acquisition. NCI can also be performed without the use of flow compensation in vessels containing slower blood flow. FIG. 1A illustrates an example of a three-dimensional radial gradient-echo pulse sequence that can be used for acquiring data using an ultra-short echo time (e.g., an echo time less than about one millisecond). FIG. 1B illustrates an example of a three-dimensional Cartesian flow-compensated gradient-echo pulse sequence that can be used for acquiring data at echo times greater than about one millisecond. As noted above, in some embodiments, the echo time can be positioned such that water and fat are substantially in phase with each other. For example, the phase difference between water and fat can be less than pi/4 radians.

After data is acquired an image is reconstructed, and this image will have very low contrast between soft tissues and relatively high contrast between calcifications and the soft tissues. Optionally, to mimic the contrast of CT, the contrast of the acquired neutral contrast MR images can be inverted so that calcifications appear bright on a darker background.

Figure 2:
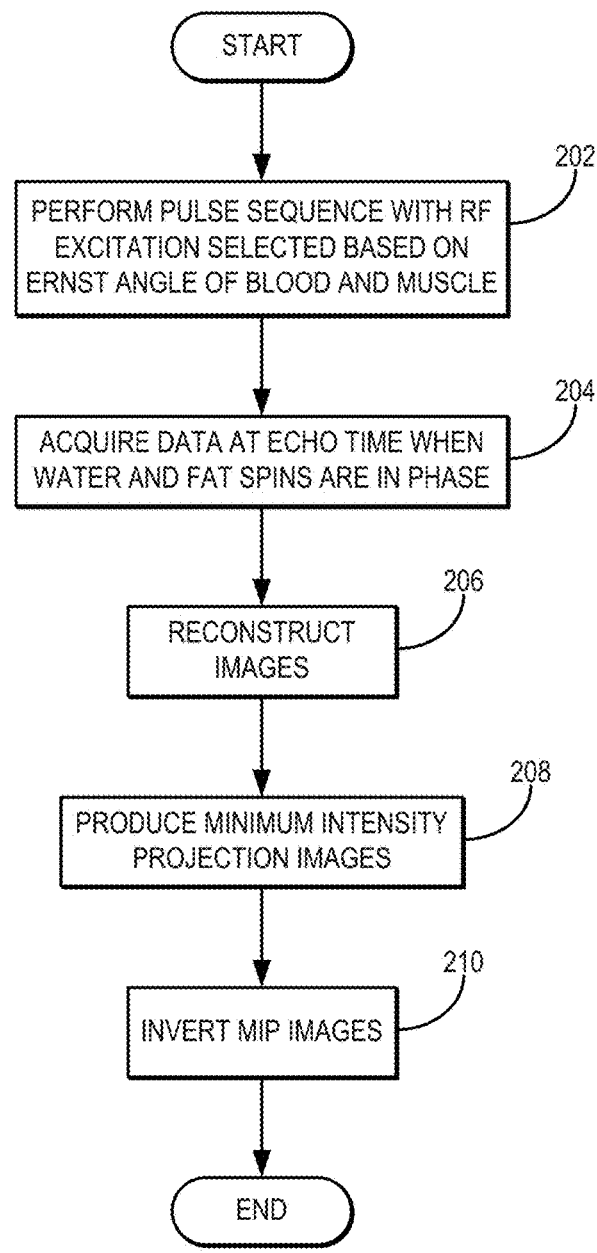
FIG. 2 is a flowchart setting forth the steps of an example method for imaging calcifications or bony structures using a neutral contrast imaging technique.

Referring now to FIG. 2, a flowchart is illustrated as setting forth the steps of an example of a method for performing neutral contrast imaging ("NCI") with a magnetic resonance imaging ("MRI") system, whereby images are obtained such that calcifications or other bony structures have significantly different image intensity values from soft tissues, which all have substantially similar image intensity values and thus neutral contrast. The method includes acquiring data from a subject using an MRI system using a pulse sequence that is specifically designed to elicit a neutral contrast in soft tissues while providing significant contrast between soft tissues and calcifications or bony structures. To this end, as described above, the method includes performing a pulse sequence in which an RF excitation pulse is generated to have a flip angle in a range from about an Ernst angle for blood to about an Ernst angle for muscle, as indicated at step 202. This RF excitation, in general, will maximize the signal intensities from blood and muscle soft tissues, which both have relatively long T1 relaxation times. As one example, assuming a T1 relaxation time of 1100 ms for muscle and 1400 ms for arterial blood, the Ernst angle, and thus the flip angle for the RF excitation, is about 5 degrees.

Data is then acquired at an echo time at which spins associated with water are substantially in-phase with spins associated with fat, as indicated at step 204. In general, the combination of this excitation technique and data acquisition timing result in soft tissues having a neutral contrast, while preserving a significant image contrast between calcifications or bony structures and the soft tissues.

In some embodiments, the data can be acquired using an ultrashort echo time ("UTE") data acquisition technique. For example, using an ultrashort TE of about 0.07 ms eliminates undesirable flow voids related to dephasing, whereas using a flip angle that is close to the Ernst angle for arterial blood minimizes flow saturation. Using an ultrashort TE acquisition also has the added benefit that sufficient signal is generated from ligaments, tendons, fascial planes, and lymph nodes, such that these tissues will become unapparent in a minimum-intensity projection image.

Images are then reconstructed from the acquired data, as indicated at step 206. The reconstructed images can be processed with a minimum-intensity projection ("MIP") algorithm, as indicated at step 208. The MIP images can then optionally be subjected to grayscale inversion to simulate the appearance of a CT image, as indicated at step 210.

In some embodiments, data can be acquired using a projection imaging technique. As one example, a 3D pointwise encoding time reduction with radial acquisition ("PETRA") imaging technique can be implemented. An example of such a pulse sequence is described by D. M. Grodzki, et al., in "Ultrashort Echo Time Imaging Using Pointwise Encoding Time Reduction with Radial Acquisition (PETRA)," *Magnetic Resonance in Medicine,* 2012; 67:510-518. Using a PETRA imaging technique, the soft tissues will all have signal intensities well above background noise levels. A notable exception is air, which has no signal intensity and thus should be edited out of the 3D-imaging volume before creating the minimum intensity projection.

The projection imaging of vascular calcifications achieved with the methods described herein is different from the approach used to create projection images with magnetic resonance angiography ("MRA"). MRA techniques are designed to render arterial blood with higher signal intensity than all other tissues, thereby allowing the use of a maximum-intensity projection algorithm to render a projection image. In order to display vascular calcifications on a projection image, however, the MRI technique described herein is designed to display the calcifications with significantly different signal intensity from all other tissues, including blood. Thus, unlike MRA techniques, the methods described here result in blood having similar image intensity values as other soft tissues, thereby resulting in a neutral contrast between blood and other soft tissues.

Using a data acquisition like PETRA, it is contemplated that arteries and veins will have similar signal intensity in most instance, but that in some instances the arteries may appear slightly darker than the veins after grayscale inversion due to inflow of less saturated spins from outside the excited volume. It is also contemplated that similar arterial inflow effects will be more pronounced using a 3D GRE acquisition because of the use of a slab-selective 3D excitation. These arterial inflow effects can advantageously improve contrast between the arterial lumen and vascular calcifications.

A method has thus been presented, in which calcifications, such as peripheral vascular calcifications, can be readily detected relative to a neutral contrast generated in soft tissues. This method allows projection images to be created with a similar appearance to CT, but without needing ionizing radiation. This imaging technique can advantageously be used to overcome a limitation of current MRI techniques; namely, the inability to reliably demonstrate vascular calcifications over a large field-of-view.

Figure 3:
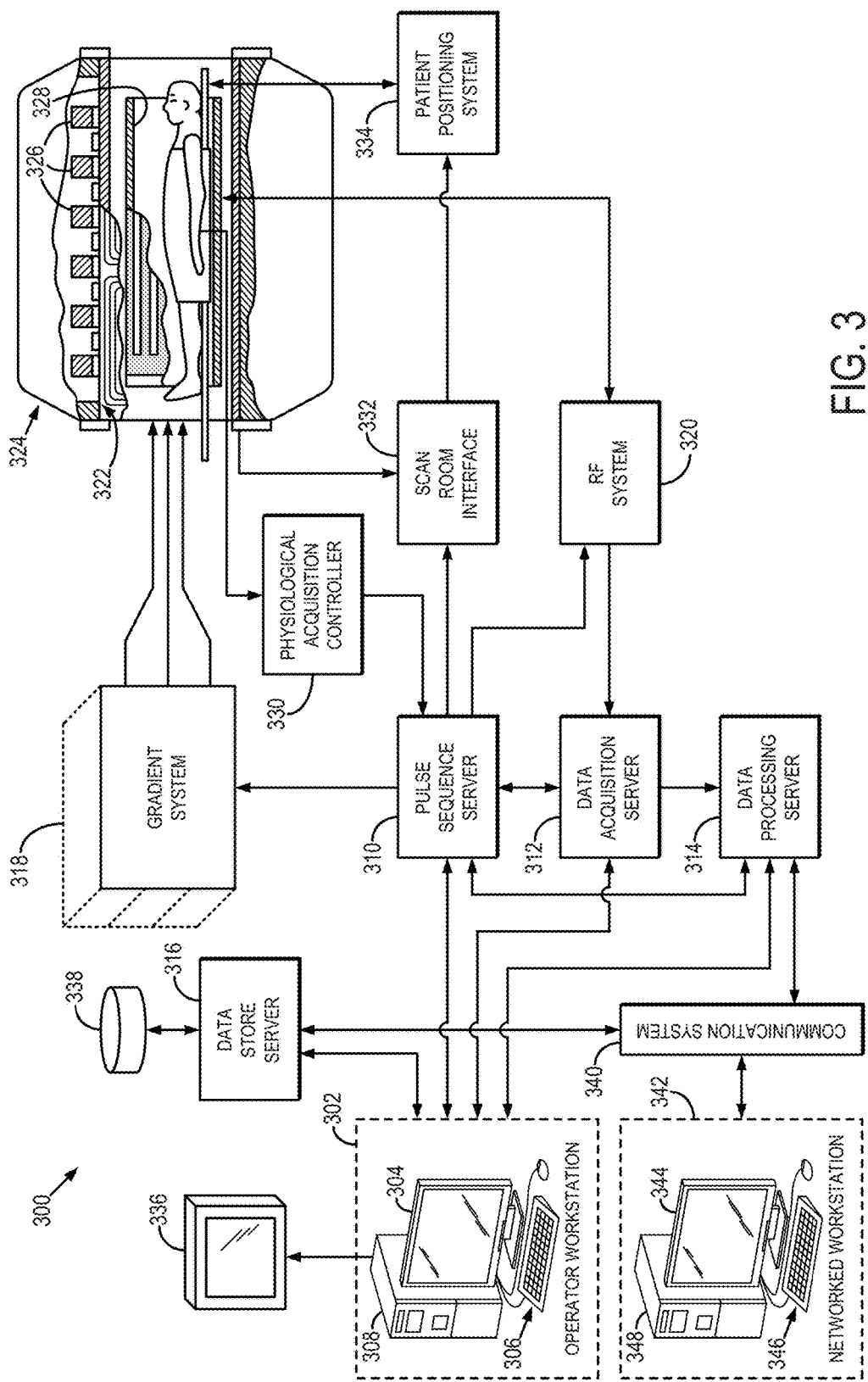
FIG. 3 is a block diagram of an example of a magnetic resonance imaging ("MRI") system.

Referring particularly now to FIG. 3, an example of a magnetic resonance imaging ("MRI") system 300 is illustrated. The MRI system 300 includes an operator workstation 302, which will typically include a display 304; one or more input devices 306, such as a keyboard and mouse; and a processor 308. The processor 308 may include a commercially available programmable machine running a commercially available operating system. The operator workstation 302 provides the operator interface that enables scan prescriptions to be entered into the MRI system 300. In general, the operator workstation 302 may be coupled to four servers: a pulse sequence server 310; a data acquisition server 312; a data processing server 314; and a data store server 316. The operator workstation 302 and each server 310, 312, 314, and 316 are connected to communicate with each other. For example, the servers 310, 312, 314, and 316 may be connected via a communication system 340, which may include any suitable network connection, whether wired, wireless, or a combination of both. As an example, the communication system 340 may include both proprietary or dedicated networks, as well as open networks, such as the internet.

The pulse sequence server 310 functions in response to instructions downloaded from the operator workstation 302 to operate a gradient system 318 and a radiofrequency ("RF") system 320. Gradient waveforms necessary to perform the prescribed scan are produced and applied to the gradient system 318, which excites gradient coils in an assembly 322 to produce the magnetic field gradients $G_x$, $G_y$, and $G_z$ used for position encoding magnetic resonance signals. The gradient coil assembly 322 forms part of a magnet assembly 324 that includes a polarizing magnet 326 and a whole-body RF coil 328.

RF waveforms are applied by the RF system 320 to the RF coil 328, or a separate local coil (not shown in FIG. 3), in order to perform the prescribed magnetic resonance pulse sequence. Responsive magnetic resonance signals detected by the RF coil 328, or a separate local coil (not shown in FIG. 3), are received by the RF system 320, where they are amplified, demodulated, filtered, and digitized under direction of commands produced by the pulse sequence server 310. The RF system 320 includes an RF transmitter for producing a wide variety of RF pulses used in MRI pulse sequences. The RF transmitter is responsive to the scan prescription and direction from the pulse sequence server 310 to produce RF pulses of the desired frequency, phase, and pulse amplitude waveform. The generated RF pulses may be applied to the whole-body RF coil 328 or to one or more local coils or coil arrays (not shown in FIG. 3).

The RF system 320 also includes one or more RF receiver channels. Each RF receiver channel includes an RF preamplifier that amplifies the magnetic resonance signal received by the coil 328 to which it is connected, and a detector that detects and digitizes the I and Q quadrature components of the received magnetic resonance signal. The magnitude of the received magnetic resonance signal may, therefore, be determined at any sampled point by the square root of the sum of the squares of the I and Q components:

$$M=\sqrt{I^2+Q^2} \quad (1);$$

and the phase of the received magnetic resonance signal may also be determined according to the following relationship:

$$\varphi = \tan^{-1}\left(\frac{Q}{I}\right). \quad (2)$$

The pulse sequence server 310 also optionally receives patient data from a physiological acquisition controller 330. By way of example, the physiological acquisition controller 330 may receive signals from a number of different sensors connected to the patient, such as electrocardiograph ("ECG") signals from electrodes, or respiratory signals from a respiratory bellows or other respiratory monitoring device. Such signals are typically used by the pulse sequence server 310 to synchronize, or "gate," the performance of the scan with the subject's heart beat or respiration.

The pulse sequence server 310 also connects to a scan room interface circuit 332 that receives signals from various sensors associated with the condition of the patient and the magnet system. It is also through the scan room interface circuit 332 that a patient positioning system 334 receives commands to move the patient to desired positions during the scan.

The digitized magnetic resonance signal samples produced by the RF system 320 are received by the data acquisition server 312. The data acquisition server 312 operates in response to instructions downloaded from the operator workstation 302 to receive the real-time magnetic resonance data and provide buffer storage, such that no data is lost by data overrun. In some scans, the data acquisition server 312 does little more than pass the acquired magnetic resonance data to the data processor server 314. However, in scans that require information derived from acquired magnetic resonance data to control the further performance of the scan, the data acquisition server 312 is programmed to produce such information and convey it to the pulse sequence server 310. For example, during prescans, magnetic resonance data is acquired and used to calibrate the pulse sequence performed by the pulse sequence server 310. As another example, navigator signals may be acquired and used to adjust the operating parameters of the RF system 320 or the gradient system 318, or to control the view order in which k-space is sampled. In still another example, the data acquisition server 312 may also be employed to process magnetic resonance signals used to detect the arrival of a contrast agent in a magnetic resonance angiography ("MRA") scan. By way of example, the data acquisition server 312 acquires magnetic resonance data and processes it in real-time to produce information that is used to control the scan.

The data processing server 314 receives magnetic resonance data from the data acquisition server 312 and processes it in accordance with instructions downloaded from the operator workstation 302. Such processing may, for example, include one or more of the following: reconstructing two-dimensional or three-dimensional images by performing a Fourier transformation of raw k-space data; performing other image reconstruction algorithms, such as iterative or backprojection reconstruction algorithms; applying filters to raw k-space data or to reconstructed images; generating functional magnetic resonance images; calculating motion or flow images; and so on.

Images reconstructed by the data processing server 314 are conveyed back to the operator workstation 302 where they are stored. Real-time images are stored in a data base memory cache (not shown in FIG. 3), from which they may be output to operator display 312 or a display 336 that is located near the magnet assembly 324 for use by attending physicians. Batch mode images or selected real time images are stored in a host database on disc storage 338. When such images have been reconstructed and transferred to storage, the data processing server 314 notifies the data store server 316 on the operator workstation 302. The operator workstation 302 may be used by an operator to archive the images, produce films, or send the images via a network to other facilities.

The MRI system 300 may also include one or more networked workstations 342. By way of example, a networked workstation 342 may include a display 344; one or more input devices 346, such as a keyboard and mouse; and a processor 348. The networked workstation 342 may be located within the same facility as the operator workstation 302, or in a different facility, such as a different healthcare institution or clinic.

The networked workstation 342, whether within the same facility or in a different facility as the operator workstation 302, may gain remote access to the data processing server 314 or data store server 316 via the communication system 340. Accordingly, multiple networked workstations 342 may have access to the data processing server 314 and the data store server 316. In this manner, magnetic resonance data, reconstructed images, or other data may exchanged between the data processing server 314 or the data store server 316 and the networked workstations 342, such that the data or images may be remotely processed by a networked workstation 342. This data may be exchanged in any suitable format, such as in accordance with the transmission control protocol ("TCP"), the internet protocol ("IP"), or other known or suitable protocols.

The present invention has been described in terms of one or more preferred embodiments, and it should be appreciated that many equivalents, alternatives, variations, and modifications, aside from those expressly stated, are possible and within the scope of the invention.

The invention claimed is:

1. A method for producing an image of a subject using a magnetic resonance imaging (MRI) system, the steps of the method comprising:
   a) directing the MRI system to generate a radio frequency (RF) excitation field to excite spins in an imaging volume, the RF excitation field having a flip angle in a range from an Ernst angle for blood to an Ernst angle for muscle;
   b) directing the MRI system to acquire data at an echo time at which spins associated with water are substantially in-phase with spins associated with fat;
   c) reconstructing an image from the acquired data, the image in which water, fat, blood, and muscle tissues have substantially similar image intensity values and calcifications have image intensity values that are significantly different from the image intensity values of the water, fat, blood, and muscle tissues in the image.

2. The method as recited in claim 1, wherein the image reconstructed in step c) depicts calcifications as dark regions and water, fat, blood, and muscle tissues as at least one of gray regions and bright regions.

3. The method as recited in claim 2, further comprising producing an inverted image by inverting the image reconstructed in step c) such that calcifications are depicted as bright regions in the inverted image.

4. The method as recited in claim 1, further comprising directing the MRI system to minimize flow-induced phase shifts in the data acquired in step b).

5. The method as recited in claim 4, wherein the MRI system is directed to minimize flow-induced phase shifts in the data acquired in step b) by acquiring the data using at least one of an ultra-short echo time data acquisition and a zero echo time acquisition.

6. The method as recited in claim 4, wherein the MRI system is directed to minimize flow-induced phase shifts in the data acquired in step b) by directing the MRI system to establish flow-compensation magnetic field gradients before directing the MRI system to acquire the data.

7. The method as recited in claim 4, wherein the MRI system is directed to minimize flow-induced phase shifts such that intravoxel flow-induced phase shifts are less than about pi/4 radians.

8. The method as recited in claim 1, wherein step b) includes acquiring data at an echo time at which a phase difference between spins associated with water and spins associated with fat is less than pi/4 radians.

9. The method as recited in claim 1, wherein step b) includes acquiring three-dimensional data and step c) includes reconstructing a three-dimensional image of the subject.

10. The method as recited in claim 9, wherein the image reconstructed in step c) has a spatial resolution finer than 8 mm$^3$.

11. The method as recited in claim 1, wherein step b) includes acquiring data by sampling at least two different signals associated with at least two different echo times.

12. The method as recited in claim 11, wherein step b) includes acquiring data from a first signal at a first echo time that is less than one millisecond and data from a second signal at a second echo time that is greater than one millisecond.

13. The method as recited in claim 1, further comprising repeating steps a)-c) for multiple different fields-of-view and producing a projection image that depicts an extended field-of-view that includes each of the multiple different fields-of-view.

14. The method as recited in claim 13, wherein the projection image is produced using a minimum intensity projection algorithm.

15. The method as recited in claim 1, wherein the calcifications comprise vascular calcifications.

* * * * *